United States Patent [19]

Kurose et al.

[11] Patent Number: 5,634,903
[45] Date of Patent: Jun. 3, 1997

[54] SYRINGE ASSEMBLY

[75] Inventors: Katsutoshi Kurose, Bear, Del.; Masaru Saiki, Kofu, Japan

[73] Assignee: Terumo Kabushiki Kaisha, Tokyo, Japan

[21] Appl. No.: 271,998

[22] Filed: Jul. 8, 1994

[30] Foreign Application Priority Data

Jul. 9, 1993 [JP] Japan ................... 5-194081

[51] Int. Cl.$^6$ ........................... A61M 5/00
[52] U.S. Cl. ................ 604/110; 604/195; 604/241
[58] Field of Search ................... 604/110, 195, 604/199, 208, 209–211, 220–222, 240, 218, 241, 242, 187

[56] References Cited

U.S. PATENT DOCUMENTS

| Re. 33,821 | 2/1992 | Banks | 604/210 |
|---|---|---|---|
| 4,850,968 | 7/1989 | Romano | 604/218 |
| 4,888,002 | 12/1989 | Braginetz et al. | |
| 4,978,340 | 12/1990 | Terrill et al. | |
| 4,986,813 | 1/1991 | Blake, III et al. | 604/240 |
| 5,112,315 | 5/1992 | Gloyer et al. | 604/195 |
| 5,188,597 | 2/1993 | Sweeney et al. | 604/110 |
| 5,215,524 | 6/1993 | Vallelunga et al. | 604/110 |
| 5,215,533 | 6/1993 | Robb | 604/110 |
| 5,263,934 | 11/1993 | Haak | 604/198 |
| 5,336,186 | 8/1994 | Haber et al. | 604/110 |
| 5,403,288 | 4/1995 | Stanners | 604/240 |
| 5,415,638 | 5/1995 | Novacek et al. | 604/240 |

FOREIGN PATENT DOCUMENTS

| 92/05821 | 4/1992 | WIPO. | |
|---|---|---|---|
| 9205821 | 4/1992 | WIPO. | |
| 9222339 | 12/1992 | WIPO | 604/264 |

*Primary Examiner*—Robert A. Hafer
*Assistant Examiner*—Ronald K. Stright, Jr.
*Attorney, Agent, or Firm*—Burns, Doane, Swecker & Mathis, LLP

[57] ABSTRACT

A syringe assembly includes a syringe body, and a plunger having a main body and a gasket mounted on its distal end portion. A needle-mounting member is detachably mounted on a distal end portion of the plunger main body. A plunger-engaging mechanism is provided on the needle-mounting member. An engaging member is provided on a distal end of the gasket, for engaging with the plunger-engaging mechanism. The needle-mounting member and the plunger further have a first structure which transmits a torque from the plunger in a direction to release an engagement between the syringe main body and the needle-mounting member to the needle-mounting member, and a second structure which releases an engagement between the engaging member and the plunger-engaging mechanism through a rotation of the plunger in a direction to keep an engagement between the needle-mounting member and the plunger main body.

8 Claims, 6 Drawing Sheets

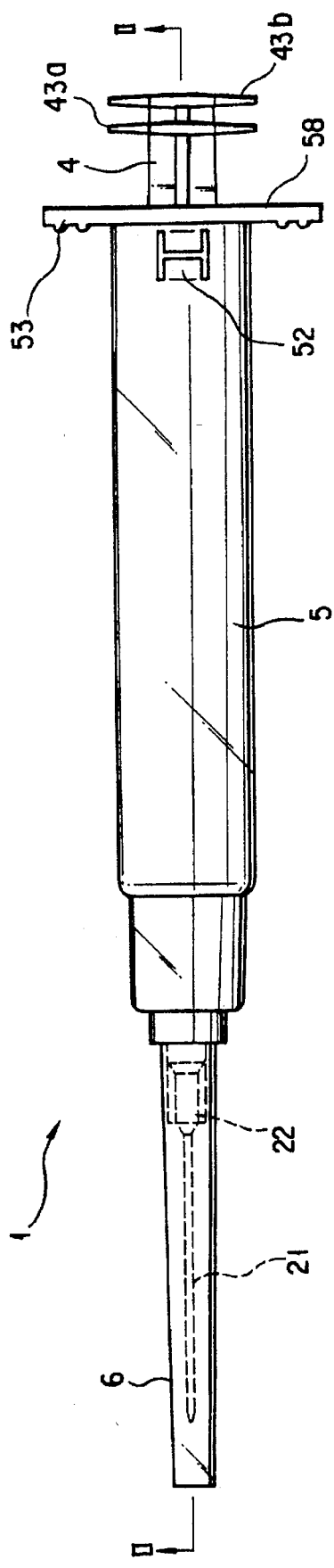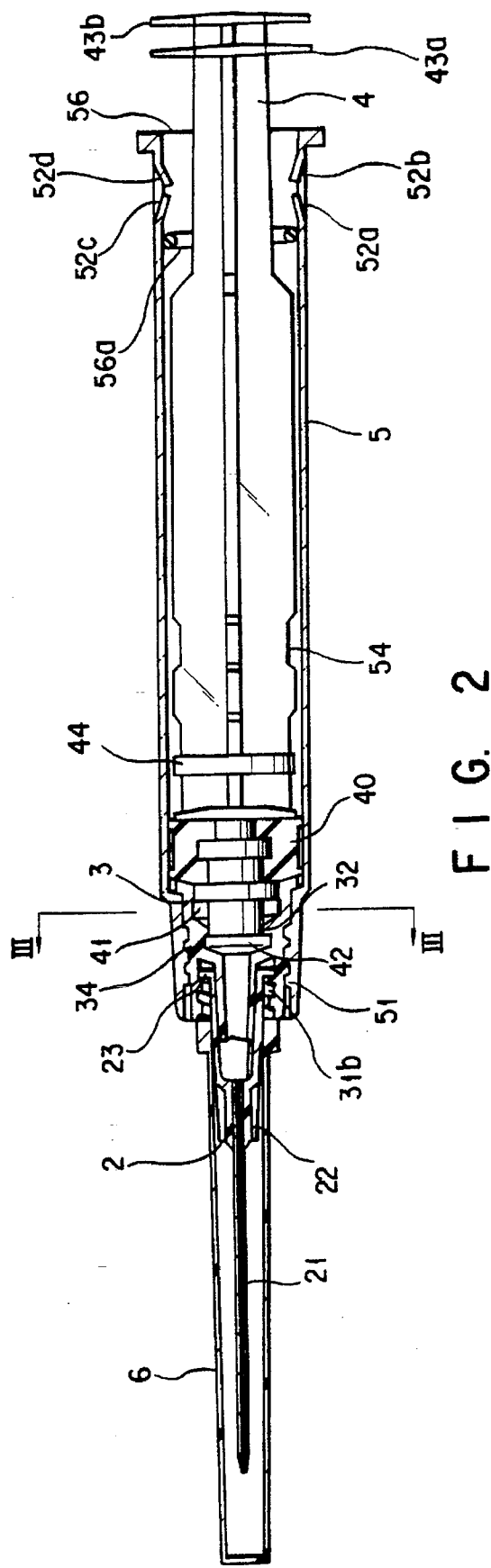
FIG. 1
FIG. 2

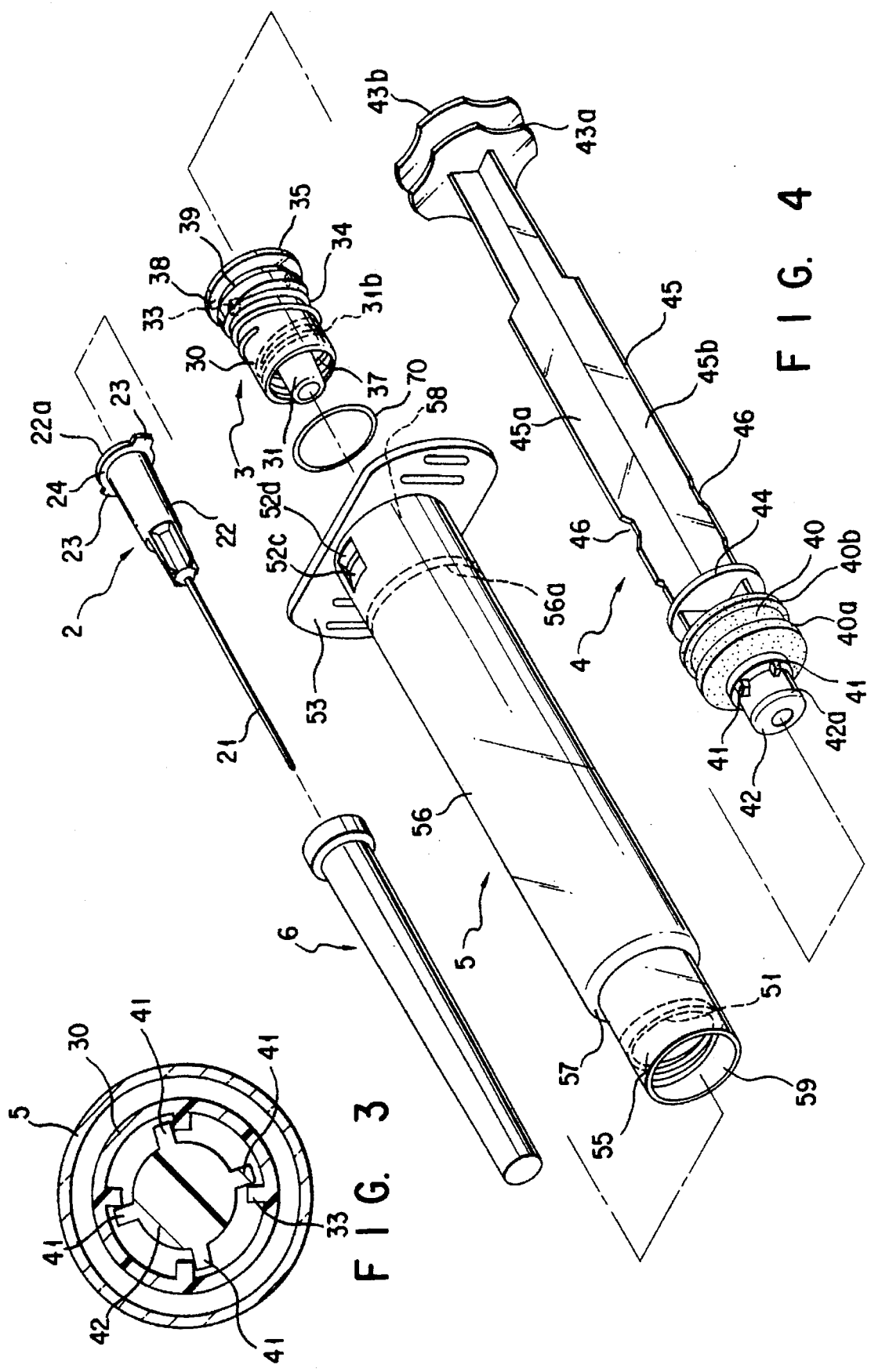

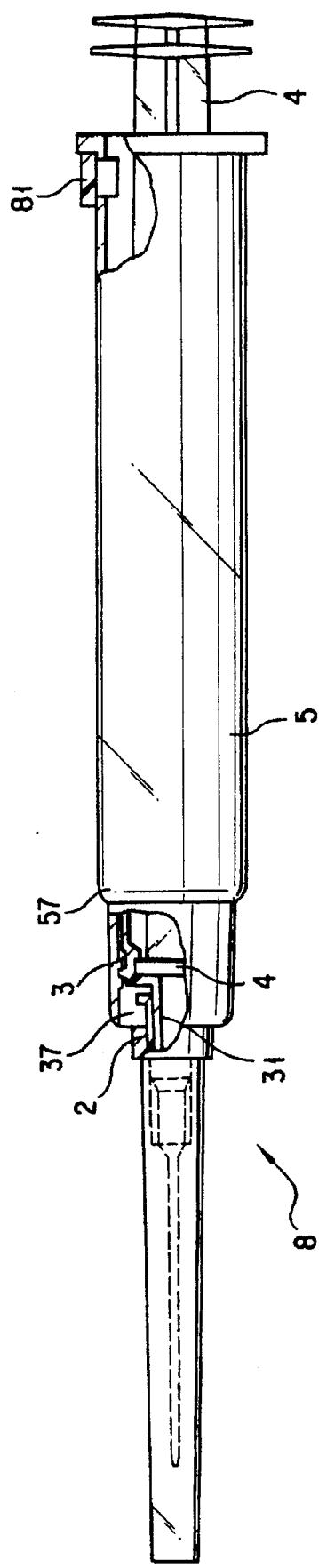
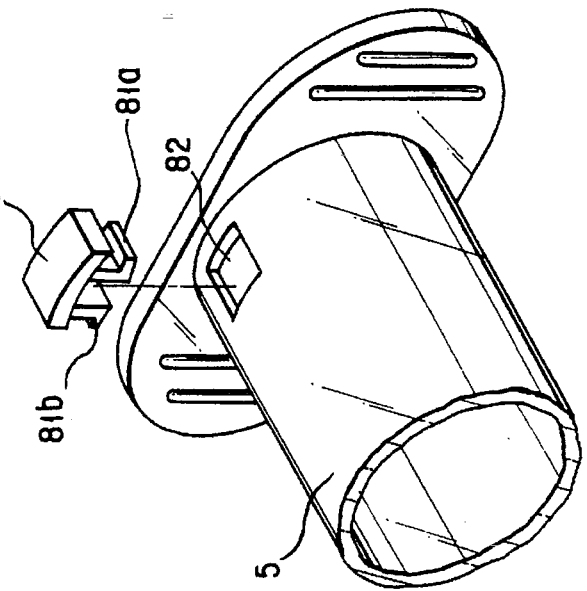
FIG. 8
FIG. 9

SYRINGE ASSEMBLY

BACKGROUND OF THE INVENTION

1. Field of the Invention

The present invention relates to a syringe assembly to be used for delivering a therapeutic liquid into a subject or for drawing blood from a subject, and more particularly to a syringe assembly which is capable of withdrawing the hypodermic needle into the syringe barrel after use.

2. Description of the Related Art

A hypodermic syringe is conventionally employed for delivering a therapeutic liquid into a subject or for drawing blood from a subject.

The hypodermic syringe generally comprises a plunger provided at its distal end with a gasket, and a cylindrical barrel provided at its distal end with a needle engaging means.

Recently, it is increasingly desired to assuredly protect therapeutic technicians from being infected with AIDS, hepatitis, and other infections. However, as a matter of fact, a syringe user sometimes have other works to do such as bleed stopping operation upon the withdrawal of a syringe, so that it is often difficult for the syringe user to pay full attention to the syringe that has been withdrawn from a subject. In such a case, the syringe having it needle tip contaminated with blood of a patient is left for a while in order to do other pressing jobs such as bleed stopping operation, and after finishing these pressing jobs the syringe user can do the capping of the needle and discard the syringe along with the capped needle.

However, when the syringe is left on a table after the withdrawal of the needle, or when the syringe falls on the floor, it may become a cause of infection from blood, or create a risk of accidental pricking of fingers due to the exposed needle.

Recently, there has been proposed a syringe provided with a needle-protecting mechanism, as shown in, for example, U.S. Pat. No. 4,978,340. The syringe proposed in this U.S. Patent comprises a syringe body, a plunger adapted to be retracted into the syringe body, and a needle carrier for engaging a needle, which is detachably mounted through thread-engagement on the distal end of the syringe body. When the plunger is rotated in the direction to release the engagement between the syringe body and the needle carrier, the rotation is transmitted to the needle carrier thereby allowing the needle carrier to be detached together with the needle from the syringe body. Accordingly, it is possible to retract the needle together with the plunger into the syringe body by sliding the plunger rearward.

Since the needle after use can be easily retracted into the syringe body in this manner, the safety of the syringe is assured.

In the above syringe, the engagement between the needle carrier and the plunger is achieved by the engagement between a hollow portion formed on the proximal end of the needle carrier as well as multiple splines formed on the inner surface of the hollow portion and a projected portion formed at the tip portion of the plunger as well as multiple splines conforming to the first mentioned multiple splines and formed on the outer circumference of the projected portion. Thus, the engagement between both of the multiple splines is achieved by inserting the projected portion of the plunger into the hollow portion of the needle carrier, and when the plunger is retracted, the needle carrier is also retracted. Further, since the multiple splines of the needle carrier and plunger are engaged together, torque of the plunger is directly transmitted to the needle carrier.

However, when the plunger is accidentally rotated in a direction which is reverse to the direction of releasing the needle carrier from the syringe body, i.e. a direction to mount the needle carrier on the syringe body (a direction which promotes the thread-engagement of the needle carrier to the syringe body), the torque resulting from this rotation is transmitted through the splines to the needle carrier. As a result, the engagement strength between the needle carrier and the syringe body becomes so large that it is sometimes becomes very difficult to disengage the needle carrier from the syringe body even if the plunger is rotated in the direction to release the engagement between the needle carrier and the syringe body.

Further, since the engagement in axial the direction between the needle carrier and the plunger is achieved through the engagement between the hollow portion of the needle carrier and the projected portion of the plunger, if the plunger is strongly pressed into the syringe body, the plunger may possibly be engaged excessively with the needle carrier, so that it becomes very difficult to move the plunger rearward in an attempt to introduce a liquid medication into the syringe. If, at this occasion, the plunger is happened to be rotated in any direction, the detachment of the needle carrier from the syringe body may be resulted in its rotation in one direction, or otherwise an excessive engagement between the needle carrier and the syringe will be resulted in its rotation in the other direction.

SUMMARY OF THE INVENTION

An object of the present invention is to provide a syringe assembly wherein an engagement between a needle-mounting member and plunger can be easily released, and even if the plunger is happened to be erroneously rotated, there is little possibility of causing the needle-mounting member to be excessively engaged with the syringe body thereby to make it very difficult to detach the needle-mounting member from the syringe body.

The above object and the other objects which will become apparent from the following detailed description have been achieved, according to the present invention, by a syringe assembly comprising:

a syringe body having an open distal end and an open proximal end, and defining therein a passage;

a plunger comprising a main body having a distal end and a proximal end, and a gasket mounted on a distal end portion of the main body, and adapted to be slidably and liquid-tightly housed in the main body of the plunger;

a needle-mounting member detachably mounted on a distal end portion of the main body of the plunger;

a plunger-engaging means provided on the needle-mounting member; and a needle-mounting member-engaging means formed on a distal end portion of the gasket, and adapted to be engaged with the plunger-engaging means;

the needle-mounting member and the plunger further comprises;

(i) a torque-transmitting means for transmitting a torque from the plunger in a direction to release an engagement between the main body of the syringe and the needle-mounting member to the needle-mounting member; and (ii) an engagement-releasing means for releasing an engagement between the needle-mounting member-engaging means and the plunger-engaging means through a rotation of the plunger in a direction to keep an engagement between the needle-mounting member and the main body of the plunger.

BRIEF DESCRIPTION OF THE DRAWINGS

FIG. 1 is a plan view showing one embodiment of the syringe assembly according to the present invention;

FIG. 2 is a cross-sectional view taken along the line II—II of FIG. 1;

FIG. 3 is a cross-sectional view taken along the line III—III of FIG. 2;

FIG. 4 is an exploded view showing the assembly of the syringe of FIG. 1;

FIG. 8 is a partially broken-away plan view showing another embodiment of the syringe assembly of the present invention;

FIG. 9 is a perspective view showing a part of the syringe assembly shown in FIG. 8;

DETAILED DESCRIPTION OF THE PREFERRED EMBODIMENT

Figure 5:
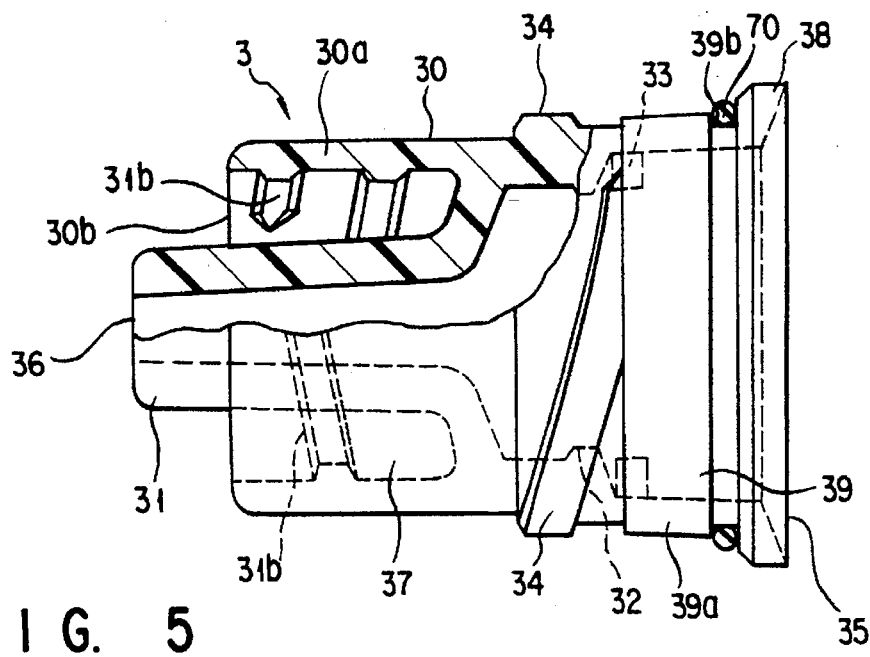
FIG. 5 is a detailed cross-sectional view showing the needle-mounting member of the syringe assembly shown in FIG. 1.

The present invention will be further explained with reference to the drawings.

Referring to FIGS. 1 to 5, one embodiment of the syringe assembly according to the present invention is illustrated therein. As shown in these drawings, the syringe assembly 1 of the present invention comprises a syringe body 5, a plunger 4 slidably disposed in the syringe body 5, and a needle-mounting member 3 detachably attached through screw-engagement to the tip end portion of the syringe body 5.

First, there will be explained about a needle 2 which will be attached to the syringe assembly of the present invention. This needle 2 may be served as being preliminarily attached to the syringe assembly 1, or served as a separate part to be attached at the moment of actual use to the syringe assembly.

The needle 2 is pierced into the body of a patient in injecting a liquid medication or in drawing blood from a patient. As is best shown in FIG. 4, the needle 2 comprises a hollow cannula 21 and a hub 22 attached to the proximal end of the cannula 21.

The cannula 21 is made of, for example, stainless steel, and has a piercing blade at its tip end. Further, the proximal end portion of the cannula 21 is inserted into the inner passage of the hollow hub 22 as shown in FIG. 2, and liquid-tightly fixed thereto with an adhesive so as not to block the hollow portion of the hub 22.

The hub 22 is cylindrical in shape, and has a proximal end constituting an opening 22a into which a hollow projected portion 31 of the needle-mounting member 3 is inserted as explained hereinafter. From the proximal end of the hub 22 is outwardly extended a round flange 24 having a pair of ribs 23 outwardly and symmetrically extending from the flange 24 in a direction perpendicular to the axis of the hub 22. These ribs 23 are adapted to be thread-engaged with the engaging thread portion 31b formed on the inner surface of the main body 30 of the needle-mounting member 3 as explained further hereinafter so as to prevent the needle 2 from being detached from the needle-mounting member 3. In the embodiment shown in this drawing, when the opening portion 22a of the hub 2 is introduced into the hollow projected portion 31 of the needle-mounting member 3, and then the needle 2 is rotated in counter-clockwise as viewed from the proximal end of the syringe, the ribs 23 of the hub 22 can be thread-engaged with the engaging thread portion 31b of the needle-mounting member 3.

The material for the hub 22 may be a thermoplastic resin, such as polypropylene, polyethylene, polycarbonate or polystyrene. It is preferable that the resin to be used therefor is more or less transparent.

In order to protect the cannula 21, a cap 6 may be used for capping the needle 2.

The syringe body 5 is formed of a hollow cylindrical body defining therethrough a passageway. The material for the syringe body may be the same as that of the hub 22, i.e. a thermoplastic resin, such as polypropylene, polyethylene, polycarbonate or polystyrene. It is also preferable that the resin to be used therefor is more or less transparent. The distal end portion 55 of the syringe body 5 is formed to have a smaller diameter (a small diameter portion 55) as compared with that of the main portion 56 (a large diameter portion). These large diameter portion 56 and small diameter portion 55 are connected to each other through a step portion 57. When the plunger 4 is pushed into the syringe body 5, an annular rib 40a of a gasket 40 attached to the plunger 4 is impinged on this step portion 57 thereby preventing the further movement of the plunger 4.

On the proximal end of the large diameter portion 56 is formed a finger tab 53 for the convenience of handling the syringe body 5 with fingers in use.

On the inner surface of the small diameter portion 55 is formed an internal or female thread 51 constituting a thread-engagement portion to be engaged with the needle-mounting member 3 as explained in detail hereinafter.

Further, a plunger-holding portion 52 is formed on the proximal end portion of the large diameter portion 56. This plunger-holding portion 52 is adapted to be engaged with the outer fringe of a round disk 44 of the plunger 4 as will be explained hereinafter so as to prevent the plunger 4 having a used needle 2 attached thereto from further moving in the axial direction thereby keeping the used needle 2 housed in the interior (a needle-housing space 54) of the syringe body 5. With this arrangement, it is possible to prevent the used needle 2 when housed within the syringe body from being exposed again out of the syringe body 5.

The plunger-holding portion 52 is formed in such a manner that at first, a slit in the form of an H is formed in the proximal end portion of the syringe body 5 thereby forming a pair of pieces 52a and 52b, or 52c and 52d, which are then bent inward thereby to form a space between pieces 52a and 52b, or a space between 52c and 52d. When the disk 44 of the plunger 4 is fitted into this space as a result of the retracting movement of the plunger 4, the movement in the axial direction of the plunger 4 is no longer possible.

The large diameter portion 56 of the syringe body 5 is also provided on its inner surface with an annular rib 56a, which is located between the distal portion thereof and the plunger-holding portion 52, and close to the plunger-holding portion 52. When the plunger 4 is retracted in an attempt to withdraw a liquid medication or blood, the round disk 44 of the plunger 4 is weakly impinged against this annular rib 56a so as to warn the user not to retract the plunger 4 any further.

The plunger 4 is slidably housed in the syringe body 5 so as to be moved in the axial direction thereof in a liquid-tight manner. At the time of use, the plunger 4 is moved in the axial direction thereof so as to withdraw or inject a liquid medication, and upon finishing such an operation, the needle 2 is housed in the interior of the syringe 5.

The plunger 4 comprises a plunger body 45 constructed with a pair of elongate plates 45a and 45b longitudinally crossing each other, and is provided on its tip end portion with a gasket 40, which is adapted to be slidably moved along the inner wall of the large diameter portion 56 of the syringe body 5. On the proximal end is provided a pair of flanges 43a and 43b to be used for pushing or drawing the plunger with fingers. The plunger body 45 may be formed from a thermoplastic resin such as polypropylene, polyethylene, polycarbonate or polystyrene.

The gasket 40 is columnar in shape and may be formed from an elastic material, such as a rubber material, for example, natural rubber, silicone rubber, isoprene rubber and the like, or an elastomeric material, for example, SBS, SEBS, polyurethane and the like. The surface of the distal end of the gasket 40 constitutes an acute-angled cone-like surface. On each of the distal end portion and the proximal end portion of the circumferential surface of the gasket 40 are formed annular ribs 40a and 40b respectively. The outer diameter of both of the annular ribs 40a and 40b is made slightly larger than the inner diameter of the large diameter portion 56 of the syringe body 5 so as to improve the liquid-tightness therebetween. Preferably, the gasket of this kind can be manufactured together with the plunger body 45 by a two-color molding method. Namely, after molding the plunger body 45 in a cavity having a space for molding the gasket 40, an elastic material is injected into the space thereby to mold the gasket 40.

On the distal end surface of the gasket 40 is mounted a columnar body 42 having a smaller diameter than that of the gasket 40, and constituting an engaging portion to be engaged with the needle-mounting member 3.

Specifically, a plurality of ribs constituting a rotation-transmitting means 41 are formed on the circumferential surface of the columnar body 42 for transmitting torque from the rotation of the plunger to the needle-mounting member 3. In the embodiment shown in the drawings, four ribs 41 are formed, each being separated by an angle of 90° (see FIG. 3).

On the circumferential surface of the distal end of the columnar body 42 is formed an annular rib 42a projecting slightly outward therefrom. When the annular rib 42a is inserted into the needle-mounting member 3 to such an extent to pass over the annular rib 32 of the needle-mounting member 3 and to extend to a portion forward of the annular rib 32, the rib 42a is caused to engage the annular rib 32. It is preferable that the outer circumferential surface of the annular rib 42a is rounded in shape, so that when the engaging portion 34 of the needle-mounting member 3 is kept thread-engaged with the internal thread 51 of the syringe 5 as shown in FIG. 4 (specifically, at the moment of retracting the plunger 4 for drawing a liquid medication or blood), the engagement of the annular rib 42a with the rib 32 can be easily released. The rib (42a) may not be annular, and may be provided as a plurality of discrete ribs, instead.

The round disk 44 is located just behind the proximal end of the gasket 40, and is adapted to be engaged with the plunger-holding portion 52 formed on the syringe body 5.

The plates 45a and 45b constituting the plunger body 45 are provided respectively with a recess 46, the location of which corresponds to the position of the proximal end of the syringe body 5 at the moment when the disk 44 of the plunger 4 is impinged on the annular rib 56a of the syringe body 5 to engage with each other. This recess 46 provides a space for allowing the plunger 4 to be extensively inclined when the plunger 4 is pressed onto the syringe body in an attempt to release the engagement between the disk 44 of the plunger 4 and the annular rib 56a of the syringe body 5.

The needle-mounting member 3 functions to detachably mount the needle 2 thereon, and, after use, to house the needle 2 within the syringe body 5 as it is retracted together with the needle 2 following the retracting movement of the plunger 4.

The needle-mounting member 3 comprises, as most clearly shown in FIG. 5, a cylindrical body 30, and a hollow projection 31 defining therein a passageway for liquid medications or blood, and being formed in integral with the cylindrical body 30. The proximal end of the hollow projection 31 is fixed to an intermediate portion of the inner wall of the cylindrical body 30, and the distal end thereof is extended out of the distal opening portion 30b of the cylindrical body 30. This hollow projection 31 is tapered so that the outer diameter thereof is gradually decreased toward its tip end, thus providing a mounting portion for allowing the hub 22 of the needle 2 to be mounted liquid-tight thereon. The shape of this tapered portion is formed so as to conform to the inner taper of the standardized hub 22.

The proximal hollow portion of the cylindrical body 30, i.e. a portion located rearward to the proximal end of the hollow projection 31, is shaped to define a space 39 for receiving the columnar body 42 of the plunger 4. On the circumference of the proximal opening 35 of the cylindrical body 30 is formed a flange 38. On the wall portion 39a defining the space 39 and near the flange 38, is formed an annular recess 39b for fitting therein an elastic O-ring 70 for improving liquid-tightness between the needle-mounting member 3 and the syringe body 5.

The cylindrical portion 30a of the cylindrical body 30 for encircling the hub-mounting member 31 is shaped, together with the outer surface of hub-mounting member 31, to define a space 37 for receiving the hub 22. On the inner wall of the cylindrical portion 30a is formed an internal thread 31b to be engaged with the hub 22. Namely, this internal thread 31b is adapted to be engaged with the rib 23 of the hub 22 so as to prevent the needle 2 from being detached from the hub-mounting member 31.

On the circumferential surface of the cylindrical body 30 of the needle-mounting member 3 is formed an external thread 34 for detachably mounting the needle-mounting member 3 on the syringe body 5, the external thread 34 being located between the central portion and the proximal end of the cylindrical body 30. This external thread 34 is adapted to be engaged with the internal thread 51 formed on the inner surface of the small diameter portion 55 of the syringe 5 so as to liquid-tightly mount the needle-mounting member 3 on the syringe body 5. This external thread 34 on the needle-mounting member 3 is shaped such that when the needle-mounting member 3 is rotated counter-clockwise as viewed from the proximal end of the syringe, the needle-mounting member 3 can be secured to the syringe.

On the inner surface of cylindrical body 30 of the needle-mounting member 3 is formed an annular rib 32, which is projecting toward the axis of the cylindrical body 30, and is adapted to be engaged with the annular rib 42a formed on the columnar body 42 of the plunger 4. This annular rib 32 is formed at the location which corresponds to where the external thread 34 is formed, but is somewhat offset toward the proximal end of the cylindrical body 30.

When it is desired, after use, to house the needle within the syringe body 5, the annular rib 32 is kept engaged with the annular rib 42a formed on the columnar body 42 of the plunger 4, and the needle-mounting member 3 with the needle 2 attached thereon is allowed to be retracted following the movement in the axial direction of the plunger 4 toward the proximal end thereof. The annular rib 32 is detachably engaged with the annular rib 42a. Specifically, the annular rib 32 is engaged with the annular rib in such a manner that when the external thread 34 of the needle-mounting member 3 is engaged with the internal thread 51 of the syringe (for example, when the plunger 4 is to be retracted for drawing a liquid medication or blood), they can be easily disengaged from each other.

Immediately behind the annular rib 32 are formed a plurality of ribs 33 which constitute a means for transmitting the torque from the plunger in cooperation with the ribs 41 formed on the columnar body 42 of the plunger 4. In the embodiment shown in the drawing, four ribs 33 projecting inward are formed on the inner surface of the columnar body 30 (see FIG. 3).

Now, the torque-transmitting means according to the present invention will be explained below.

When the plunger 4 is rotated, the side surfaces of the ribs 33 of the needle-mounting member 3 are impinged upon the side surfaces of the ribs 41 of the plunger 4, so that the torque from the plunger 4 is transmitted to the needle-mounting member 3, thereby causing the needle-mounting member 3 to rotate following the rotation of the plunger 4. In this manner, a torque resulting from the rotation of plunger 4 in either directions can be transmitted to the needle-mounting member 3 through these torque transmitting means, namely, ribs 41 and 33.

Therefore, if the engagement between the syringe body 5 and the needle-mounting member 3 is happens to be loosened at the time of using the syringe, the engagement can be restored or strengthened by rotating the needle-mounting member 3 through the rotation of the plunger 4 in a prescribed direction.

Figure 7:
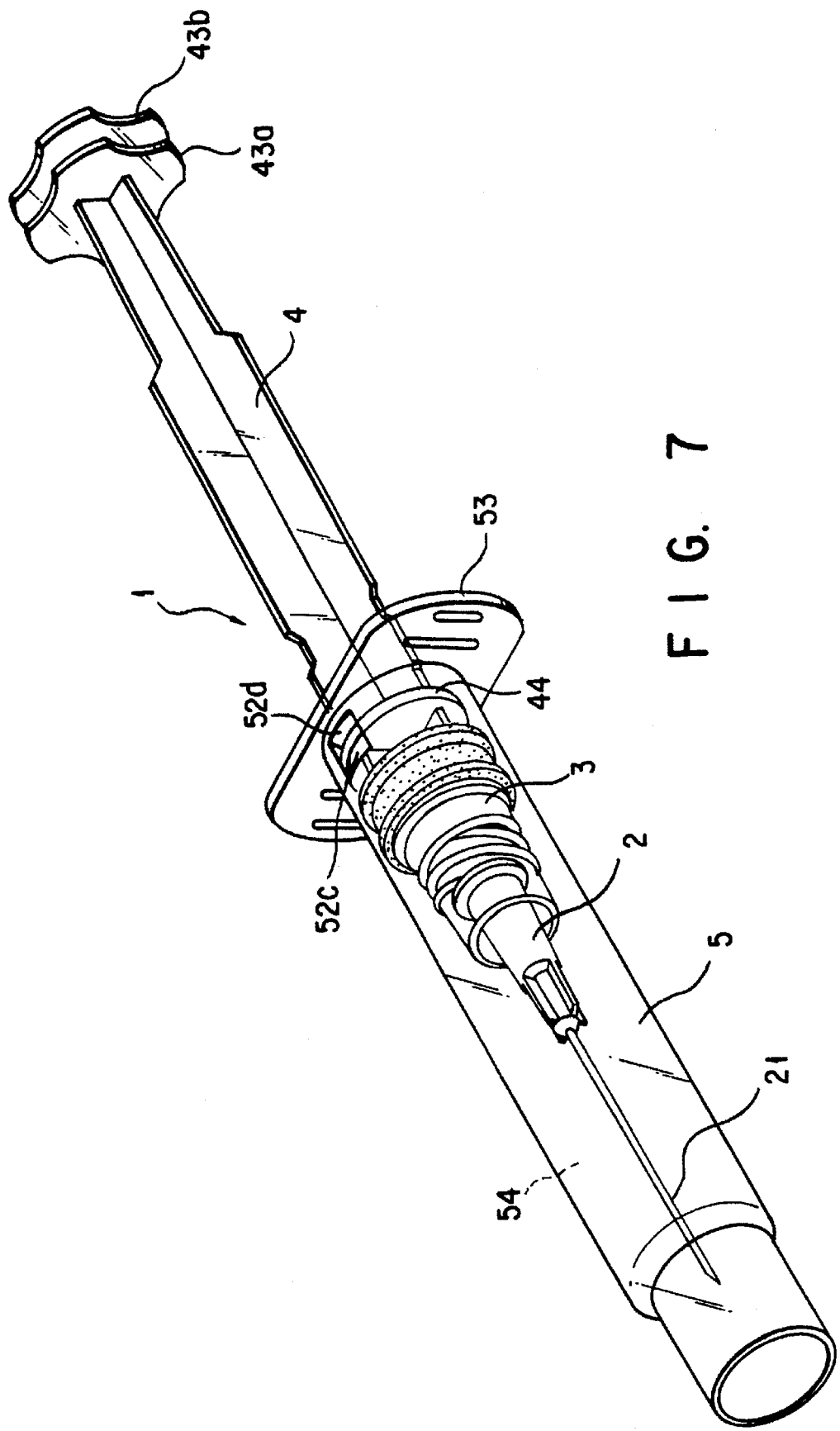
FIG. 7 is a perspective view showing the syringe assembly having a needle housed therein, according to the present invention.

After the use of the syringe, the plunger 4 is caused to be engaged with the engaging portion of the needle-mounting member 3, and at the same time the plunger 4 is rotated in such a direction that allows the release of the engagement between the external thread 34 of the needle-mounting member 3 and the internal thread 51 of the syringe body 5, thereby causing the needle-mounting member 3 to rotate in the counter-clockwise direction and releasing the engagement between the external thread 34 and the internal thread 51, and then the plunger 4 is retracted thereby causing the needle 2 to be housed within the syringe 2 as shown in FIG. 7.

In the embodiment shown in the drawing, the engaging mechanism (thread-engagement) between the needle-mounting member 3 and the syringe body 5 is reverse in engaging direction as compared with the engaging mechanism (thread-engagement) between the needle-mounting member 3 and the hub 22 of the needle 2. Accordingly, when the needle 2 is inserted into the 5 space 37 of the needle-mounting member 3 while rotating the needle 2 so as to engage the hub 22 with the internal thread 31b of the needle-mounting member 3, the needle 2 is caused to be fully engaged with the needle-mounting member 3. At this moment, if the rotation of the needle 2 is further continued beyond this point, the torque resulting from this rotation of the needle 2 is transmitted to the needle-mounting member 3 thereby causing the needle-mounting member 3 to rotate, and at the same time causing a strengthening of the engagement between the needle-mounting member 3 and syringe 5 due to the rotation of the needle-mounting member 3. Therefore, if the engagement between the syringe body 5 and the needle-mounting member 3 happens to be loosened at the time of using the syringe, the engagement can be restored or strengthened by rotating the needle 2 in a prescribed direction.

Next, there will be explained about the means for releasing the engagement between the needle-mounting member-engaging portion 42 provided on the plunger 4 and the plunger-engaging portion 32 provided on the needle-mounting member 3. This engagement-releasing means is arranged with an aim to release the engagement between the plunger 4 and the needle-mounting member 3 so as not to transmit the torque of the plunger 4 to the needle-mounting member 3 in the occasion where the plunger 4 is erroneously rotated in the direction that will cause an excessive engagement between the external thread 34 provided on the needle-mounting member 3 and the internal thread 51 provided on the syringe body 5. If the external thread 34 provided on the needle-mounting member 3 is excessively engaged with the internal thread 51 provided on the syringe body 5, the operation of releasing the engagement may become very difficult.

Figure 6A:
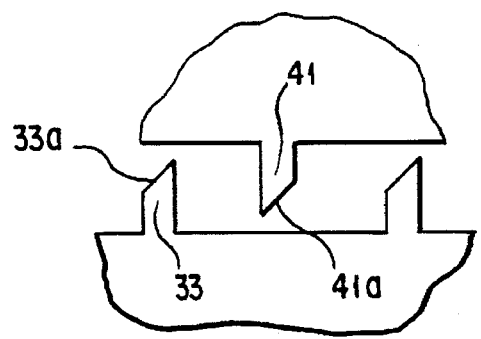
FIGS. 6A to 6C illustrate a torque transmitting means and an engagement-releasing means between the plunger and the needle-mounting member of the present invention.
Figure 6B:
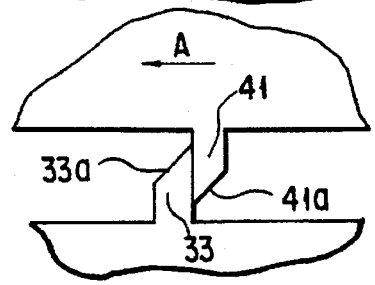
Figure 6C:
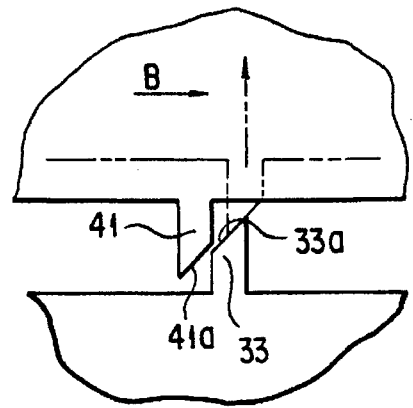

FIGS. 6A to 6C illustrate a plunger-engagement-releasing means, which comprises a tip portion 33a of the torque-transmitting portion (rib) 33 formed on the needle-mounting member 3, and the tip portion 41a of the torque-transmitting portion (rib) 41 formed on the plunger 4.

Namely, the tip portion 33a of the torque-transmitting portion (rib) 33 formed on the needle-mounting member 3 constitutes a slant surface having a prescribed angle in relation to the axial direction of the syringe, while the tip portion 41a of the torque-transmitting portion (rib) 41 mounted on the plunger 4 constitutes a slant surface having the same angle as that of the tip portion 33a. The angle of the slant surface 33a or 41a may preferably be in the range of 20 to 80 degrees, more preferably in the range of 45 to 60 degrees.

It is preferable to form the slant surface on both of the torque-transmitting portions 33 and 41 as described above, but the slant surface may be formed on only one of them.

As shown in FIG. 6C, when the plunger 4 is rotated in the direction indicated by an arrow B (i.e., a direction which promotes the engagement between the external thread 34 formed on the needle-mounting member 3 and the internal thread 51 formed on the syringe body 5), the engagement-releasing slant surface 41a formed on the plunger 4 is impinged upon the engagement-releasing slant surface 33a formed on the needle-mounting member 3 thereby deviating the direction of torque from the plunger 4, thus transmitting a very weak torque to the needle-mounting member 3. If there is a resistance on the part of the needle-mounting member 3 at this moment (or if the needle-mounting member 3 is engaged with the syringe body 5), the engagement-releasing slant surface 41a moves sliding over the engagement-releasing slant surface 33a. As a result, the plunger 4 is slightly retracted thereby releasing the engagement between the engaging portion 42 formed on the tip portion of the plunger 4 and the engaging portion 32 formed on the inner surface of the needle-mounting member 3. Therefore, even if the plunger 4 is rotated in the direction indicated by the arrow B, the resulting torque is no more transmitted to the needle-mounting member 3.

Further, as shown in FIG. 6B, when the plunger 4 is rotated in the direction indicated by an arrow A, which is opposite to the direction of the arrow B, (i.e., a direction which releases the engagement between the external thread 34 formed on the needle-mounting member 3 and the internal thread 51 formed on the syringe body 5), the torque-transmitting portion 33 formed on the needle-mounting member 3 is impinged upon the flat side surface of the torque-transmitting portion 41 of the plunger 4, so that the engagement-releasing slant surface 33a would never impinge on the engagement-releasing slant surface 41a. Accordingly, the torque given in the direction of A by the plunger 4 is reliably transmitted to the needle-mounting member 3. Moreover, even if the plunger 4 is rotated in the direction of A, the engagement between the engaging portion 42 formed on the tip portion of the plunger 4 and the engaging portion 32 formed on the inner surface of the needle-mounting member 3 would never be released.

In the embodiment shown in the drawing, when the plunger 4 is rotated counter-clockwise as viewed from the proximal end of the syringe, the external thread 34 is rendered to be engaged with the internal thread 51 thereby achieving the attachment of the needle-mounting member 3 to the syringe body 5. If on the contrary the plunger 4 is rotated clockwise, the engagement between the external thread 34 and the internal thread 51 is released, and the rib 32 is engaged with rib 42, thereby rendering the needle 2 ready to be housed within the needle-housing space 54 of the syringe body 5.

Now, the method of assembling the syringe assembly of the present invention will be explained with reference to FIG. 4.

First, after attaching the 0-ring 70 to the needle-mounting member 3, the needle-mounting member 3 with its hollow projected portion 31 being directed forward is introduced into the syringe body 5 through the proximal opening 58 thereof.

Then, the distal portion of the plunger 4 is inserted into the opening 35 of the needle-mounting member 3, and while keeping this state, the plunger 4 is pushed down to the distal end portion of the syringe 5.

Thereafter, the plunger 4 is rotated half a revolution counter-clockwise while pressing the plunger 4 toward the distal end of the syringe 5 with a weak force. As a result, the torque-transmitting portion 33 formed on the inner surface of the needle-mounting member 3 is caused to be engaged with the torque-transmitting portion 41 formed on the tip end portion of the plunger 4, and at the same time the needle-mounting member 3 is rotated following the rotation of the plunger 4. When the needle-mounting member 3 is rotated in this manner, the external thread 34 of the needle-mounting member 3 is engaged with the internal thread 51 of the syringe 5, thereby disposing the needle-mounting member 3 in the syringe 5 with the distal end portion of the needle-mounting member 3 being pressed in a liquid-tight manner on the inner surface of distal end portion of the syringe 5. At the same time, the O-ring 70 is impinged on the inner surface of the syringe body 5, improving the liquid tightness therebetween.

Subsequently, the hub 22 of the needle 2 is inserted into the space 37 formed between the hollow body 31 projecting slightly from the distal opening 59 of the syringe body 5 and the cylindrical body 30 of the needle-mounting member 3, and then the needle 2 is rotated half a revolution clockwise while pressing the needle 2 toward the proximal end thereof. As a result, the rib 23 formed on the proximal end of the hub 22 of the needle 2 is engaged (luer-locked) with the internal thread 31b of the needle-mounting member 3, thereby mounting the needle 2 on the needle-mounting member 3.

Finally, the protecting cap 6 is capped on the needle 2.

The method of using the syringe assembly of the present invention will now be explained below.

The syringe assembly of the present invention may be provided as a product with the needle 2 being preliminarily attached to the syringe assembly, or provided as a product without the needle 2 attached thereto, as described earlier. In the latter case, the needle 2 can be attached when the syringe assembly is actually used.

In order to mount the needle on the syringe at the moment of use, the protecting cap 6 attached to the needle as shown in FIG. 1 or FIG. 2, is rotated clockwise as viewed from the distal end of the syringe, so as to mount the needle on the needle-mounting member 3 through thread-engagement. In this occasion, since the engaging mechanism (thread-engagement) between the needle-mounting member 3 and the syringe body 5 is in reverse engaging direction as compared with the engaging mechanism (thread-engagement) between the needle-mounting member 3 and the hub 22 of the needle 2, when the needle 2 is inserted into the space 37 of the needle-mounting member 3 while rotating the needle 2, the engagement between the external thread 34 formed on the needle-mounting member 3 and the internal thread 51 formed on the syringe body 5 will be further strengthened.

In use, the cap 6 is removed, the plunger 4 is retracted, the needle 2 is pierced into a container such as a vial containing a liquid medication, and then the plunger 4 is further retracted for drawing the liquid medication into the vial. As the plunger 4 is retracted, the round disk 44 of the plunger 4 is caused to impinge upon the annular rib 56a formed on the inner surface of the syringe 5, thereby warning the user not to retract the plunger any further.

Upon finishing the drawing of the liquid medication, the plunger 4 is moved toward its distal end thereby removing air within the syringe, and then the needle 2 is pierced into the skin of a patient in order to deliver the liquid medication into the patient by pushing the plunger 4 toward the distal end of the syringe body 5. When the distal end of the gasket 40 of the plunger 4 is impinged on the step portion 57 of the syringe body 5, the administration of the liquid medication is finished (the state as shown in FIG. 1 or FIG. 2).

After finishing the administration of the liquid medication, the needle 2 is withdrawn from the patient, and then the plunger 4 is rotated clockwise as viewed from the proximal end of the syringe while weakly pressing the plunger 4 toward the distal end thereof. As a result, the torque-transmitting portion 33 formed on the inner surface of the needle-mounting member 3 is impinged upon the torque-transmitting portion 41 formed on the tip end portion of the plunger 4, and at the same time the needle-mounting member 3 is rotated following the rotation of the plunger 4. When the needle-mounting member 3 is rotated in this manner, the engagement between the external thread 34 of the needle-mounting member 3 and the internal thread 51 of the syringe 5 is released. At this moment, the engagement between the needle-mounting member 3 having the needle 2 attached thereto and the plunger 4 is not released, but kept as it is.

Therefore, when the plunger 4 is retracted, the needle 2 attached to the needle-mounting member 3 is housed within the inner space 54 of the syringe body 5 together with the plunger 4 having the needle-mounting member 3 engaged therewith.

Specifically, when the disk 44 of the plunger 4 is impinged upon and engaged with the annular rib 56a formed on the inner wall of the syringe body 5 during retracting movement of the plunger 4, the plunger 4 is then pressed against the inner wall of the syringe body 5 so as to release the engagement between the disk 44 and 56a as mentioned above, thereby allowing the plunger 4 to be retracted further.

When the plunger 4 is further retracted, the circumferential portion of the disk 44 of the plunger 4 is caused to fall into a space between the stopper pieces 52a and 52b, as well as into a space between the stopper pieces 52c and 52d. As a result, the plunger 4 is fixed to the syringe body 5 (FIG. 7), and the movement in the axial direction of the plunger 4 is rendered no more possible.

As explained above, it is possible according to the syringe assembly of the present invention to house the needle 2 within the syringe body 5 without directly touching the needle 2. Further, it is also possible to easily achieve the engagement between the needle-mounting member 3 and syringe body 5 by simply rotating the plunger 4. Since the plunger having the needle 2 attached thereto is fixed to the syringe body 5 with the needle being housed within the syringe body 5 after use, there is no possibility of the needle 2 itself or blood adhered to the needle being exposed out of the syringe body 5 thereby assuring the safety in handling it. Since the tip portion (blade portion) of the needle 2 is not exposed out of the syringe 5, there is no possibility of user's fingers being pricked in the process of covering the needle with a cap 6.

FIGS. 8 and 9 illustrate another embodiment of the syringe assembly according to the present invention. The syringe assembly 8 shown therein is the same in construction except that the hub-engaging portion (an internal thread) 31b is not formed on the inner surface of the cylindrical portion 30 of the needle-mounting member 3, or that the plunger-engaging portion is provided by a separate stopper member 81.

In the syringe 8, the needle 2 can be attached to the needle-mounting member 3 by simply inserting it into the space 37 and pushing it toward the proximal end of the needle-mounting member 3 (in the rightward in FIG. 8).

Further, an opening 82 is formed near the proximal end of the syringe body 5. The stopper member 81 comprises a pair of stopper pieces 81a and 81b, and is inserted into the opening 82. Namely, the pair of stopper pieces 81a and 81b are adapted to be fitted into a space formed between the gasket 40 and disk 44, thereby preventing the movement in axial direction of the plunger 4.

Figure 10:
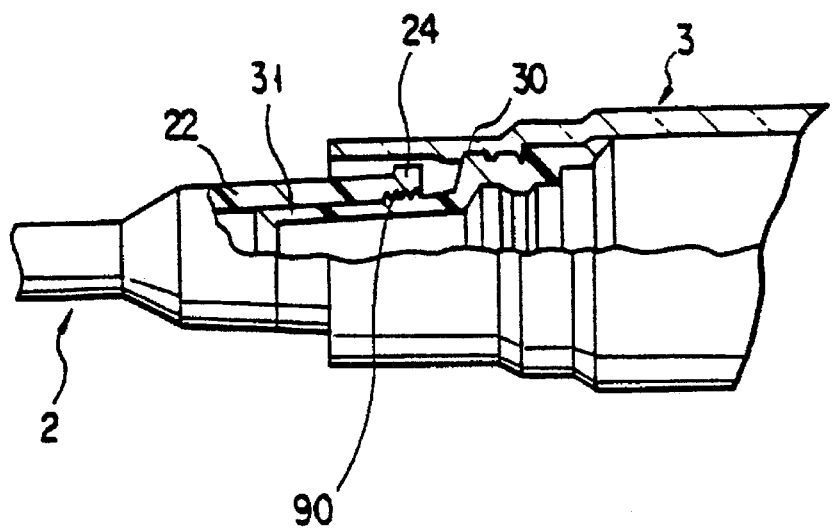
FIG. 10 illustrates part of the syringe assembly according to still another embodiment of the present invention.

FIG. 10 illustrates another embodiment of the present invention wherein the engagement between the hub 22 of the needle 2 and the needle-mounting member 3 is realized not through the above luer-lock mechanism, but through the engaging mechanism (threaded engagement) 90 comprising a thread formed on the inner surface of the flange 24 of the hub 22, and a corresponding thread formed on the outer surface of the hollow projected portion of the needle-mounting member 3. Other constituents are the same as those of the above embodiment. The structure of this syringe assembly is applicable in particular to a syringe of small capacity (for example 3 ml).

In either of above embodiments, both of a torque-transmitting means for transmitting the rotation of the plunger in the direction to release the engagement between the syringe body 5 and the needle-mounting member 3 to the needle-mounting member 3; and an engagement-releasing means for releasing the engagement between the needle-mounting member-engaging means and the plunger-engaging means through the rotation of the plunger in the direction to keep the engagement between the needle-mounting member and the syringe body are constructed with a side surface disposed substantially in parallel with the axial direction of the syringe, a plurality of ribs formed on the tip portion of the plunger and having a slant surface inclined in relative to the axial direction of the syringe, and a plurality of ribs formed on the needle-mounting member 3. However, the constructions of these torque-transmitting means and engagement-releasing means are not limited to above embodiments. These torque-transmitting means and engagement-releasing means may be composed of, for example, a one-way clutch mechanism formed on the distal end face of the columnar body 42 of the plunger, and a clutch mechanism which is formed, in conformity with the above one-way clutch mechanism, on the inner surface of the needle-mounting member 3 on which the distal end surface of the columnar body 42 is impinged.

Figure 11A:
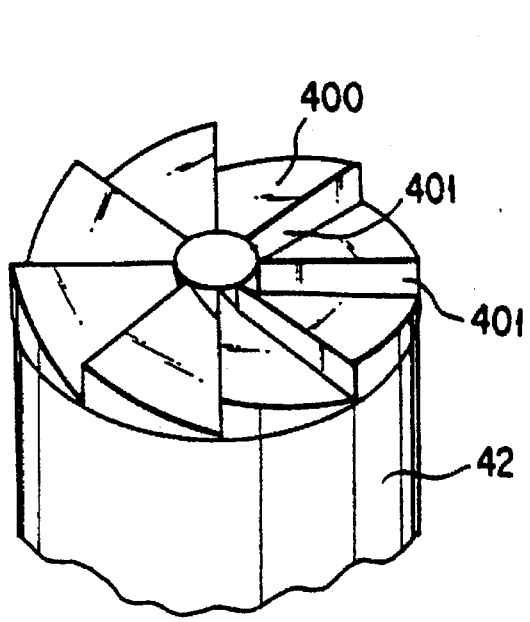
FIGS. 11A and 11B illustrate another torque transmitting means and engagement-releasing means between the plunger and the needle-mounting member of the present invention.
Figure 11B:
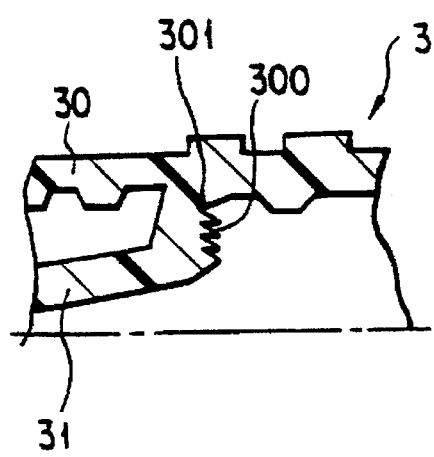

FIGS. 11A and 11B illustrate this one-way clutch mechanism. As shown in FIG. 11A, the clutch mechanism comprising a plurality of slant surfaces 400 inclined in relative to the flat surface perpendicular to the axis of the columnar body 42, and side surfaces 401, each being disposed between the above slant surfaces 400 and in perpendicular to the above-mentioned flat surface is formed on distal end surface of the columnar body 42 of the plunger. On the other hand, as shown in FIG. 11B, a corresponding clutch mechanism is provided on the face of the connecting portion between the cylindrical body 30 of the needle-mounting member 3 and the hollow projecting portion 31. It comprises slant surfaces 300 corresponding to the slant surfaces 400, and perpendicular surfaces 301 corresponding to the side surfaces 401. The slant surfaces 400 face the slant surfaces 300, and the perpendicular side surfaces face the surfaces 301. When the plunger is rotated in a direction in which the perpendicular side surfaces 401 and 301 are impinged upon with each other, the torque resulting from the rotation is transmitted to the needle-mounting member 3. On the other hand, when the plunger is rotated in the opposite direction, the slant surfaces 400 slide over the slant surfaces 300, thereby releasing the engagement between the plunger and the needle-mounting member.

What is claimed is:

1. A syringe assembly which comprises:

a syringe body having an open distal end and an open proximal end, and defining therein a passage;

a plunger comprising a main body having a distal end and a proximal end, and a gasket mounted on a distal end portion of said main body and adapted to be slidably and liquid-tightly housed in said syringe body, the distal end of said plunger defining a columnar body that is located distally of the gasket;

a needle-mounting member for having threadably mounted therein a needle, said needle-mounting member being detachably screwed into a distal end portion of said syringe body;

plunger-engaging means provided on said needle-mounting member; and needle-mounting member-engaging means formed adjacent a distal end portion of said gasket, and adapted to be engaged with said plunger-engaging means;

said needle-mounting member and said plunger further comprising:

(i) torque-transmitting means for transmitting torque from said plunger to said needle-mounting member in a direction to release an engagement between said syringe body and said needle-mounting member, said torque transmitting means including a plurality of first ribs formed on said columnar body and a plurality of second ribs formed on said needle-mounting member, each of said first ribs having a side surface which is substantially parallel to an axial direction of said main body, each of said second ribs having a side surface which impinges upon said side surface of one of the first ribs when the plunger is rotated in a direction to release engagement between said syringe body and said needle-mounting member to thereby transmit torque from the plunger to the needle-mounting member; and (ii) engagement-releasing means for releasing an engagement between said needle-mounting member-engaging means and said plunger-engaging means through rotation of said plunger in a direction which maintains engagement between said needle-mounting member and said syringe body, said engagement-releasing means including a plurality of first slant surfaces and a plurality of second slant surfaces, said first slant surfaces being disposed on said first ribs and being inclined with respect to said side surfaces on said first ribs, said second slant surfaces being disposed on said second ribs and being inclined with respect to said side surfaces on said second ribs, said first slant surfaces being movable over the second slant surfaces when said plunger is rotated in a direction for maintaining engagement between said needle-mounting member and said syringe body to release engagement between the needle-mounting member-engaging means and said plunger-engaging means.

2. The syringe assembly according to claim 1, wherein said plunger body has an engagement member for engaging with said syringe body, and said syringe body has, near its proximal end, engaging means for engaging said engagement member of said plunger body to stop movement of said plunger in an axial direction when said plunger is retracted within said syringe body after use of the syringe.

3. The syringe assembly according to claim 2, wherein said engagement member of said plunger body comprises a round disk provided on the plunger body at a position nearer to the proximal end of said plunger than said gasket, and said engaging means on said syringe body comprises at least one pair of cut pieces inwardly bent toward an inside of the syringe body and defining a space therebetween into which said round disk is fitted.

4. The syringe assembly according to claim 3, wherein said syringe body has an annular rib inwardly projecting therefrom at a position nearer to the distal end than said engaging means, said annular rib temporarily engaging the round disk when said plunger is retracted within said syringe body during use of the syringe assembly.

5. The syringe assembly according to claim 4, wherein said plunger has a recess at a position corresponding to the proximal end of said syringe body when said annular rib on said syringe body engages said round disk, said recess abutting said syringe body when said plunger is pressed against said syringe body to release the engagement between said annular rib on said syringe body and said round disk on said plunger.

6. The syringe assembly according to claim 1, wherein a direction in which said needle-mounting member is screwed into said syringe body is opposite to a direction in which said needle-mounting member is adapted to have threaded thereon the needle.

7. The syringe according to claim 1, wherein said plunger body and said gasket are two-color molded with the gasket being made of an elastic material.

8. The syringe according to claim 1, wherein said needle-mounting member-engaging means is provided on said columnar body.

* * * * *

UNITED STATES PATENT AND TRADEMARK OFFICE
CERTIFICATE OF CORRECTION

PATENT NO. : 5,634,903
DATED : June 3, 1997
INVENTOR(S) : Katsutoshi KUROSE et al It is certified that error appears in the above-indentified patent and that said Letters Patent is hereby corrected as shown below:

In Column 7, line 41, after "3" delete "is".

In Column 7, line 65, delete "5".

Signed and Sealed this

Eleventh Day of November, 1997

Attest:

BRUCE LEHMAN

Attesting Officer

Commissioner of Patents and Trademarks